United States Patent [19]
Sagel et al.

[11] Patent Number: 5,891,453
[45] Date of Patent: Apr. 6, 1999

[54] DELIVERY SYSTEM FOR A TOOTH WHITENER USING A STRIP OF MATERIAL HAVING LOW FLEXURAL STIFFNESS

[75] Inventors: Paul Albert Sagel, Mason; Robert Stanley Dirksing, Cincinnati; Frederick James Rohman, Maineville, all of Ohio

[73] Assignee: The Procter & Gamble Company, Cincinnati, Ohio

[21] Appl. No.: 40,000

[22] Filed: Mar. 17, 1998

Related U.S. Application Data

[63] Continuation-in-part of Ser. No. 870,330, Jun. 6, 1997.

[51] Int. Cl.$^6$ ............... A61K 6/02; A61K 7/16; A61K 7/20; A61K 33/40
[52] U.S. Cl. ............... 424/401; 424/49; 424/53; 424/613
[58] Field of Search ............ 433/215; 424/401, 424/49–58

[56] References Cited

U.S. PATENT DOCUMENTS

| | | | |
|---|---|---|---|
| 3,955,281 | 5/1976 | Weitzman | 32/14 |
| 4,138,814 | 2/1979 | Weitzman | 32/14 |
| 4,324,547 | 4/1982 | Arcan et al. | 433/71 |
| 4,728,291 | 3/1988 | Golub | 433/215 |
| 4,741,941 | 5/1988 | Englebert et al. | 128/71 |
| 4,786,253 | 11/1988 | Morais | 433/60 |
| 4,799,888 | 1/1989 | Golub | 433/215 |
| 4,900,554 | 2/1990 | Yanagibashi et al. | 424/448 |
| 5,166,233 | 11/1992 | Kuroya et al. | 524/37 |
| 5,310,563 | 5/1994 | Curtis et al. | 424/616 |
| 5,326,685 | 7/1994 | Gaglio et al. | 433/215 |
| 5,340,314 | 8/1994 | Tarius | 433/168.1 |
| 5,560,379 | 10/1996 | Pieczenik | 132/329 |
| 5,639,445 | 6/1997 | Curtis et al. | 404/49 |
| 5,713,738 | 2/1998 | Yarborough | 433/215 |

FOREIGN PATENT DOCUMENTS

| | | | |
|---|---|---|---|
| Sho 63-54318 | 3/1988 | Japan | A61K 9/70 |
| Hei 10- 17448 | 1/1998 | Japan | A61K 7/16 |
| 2 108841A | 5/1983 | United Kingdom | A61K 9/24 |
| WO 97/25968 | 7/1997 | WIPO | A61K 7/22 |

*Primary Examiner*—Shep K. Rose
*Attorney, Agent, or Firm*—Angela Marie Stone; Betty J. Zea

[57] ABSTRACT

A system for delivering a tooth whitening substance to a plurality of adjacent teeth, the delivery system comprising a strip of flexible material having a sufficient flexibility to form a curved shape on a plurality of adjacent teeth and a tooth whitening substance. The strip of material is readily conformable to the teeth surfaces and to interstitial tooth spaces without permanent deformation when the delivery system is placed thereagainst. The tooth whitening substance is applied to the strip of material such that when the delivery system is placed on the surface of the teeth, the substance contacts the surface providing an active onto the surface. The substance also provides adhesive attachment between the strip of material and the surface to hold the delivery system in place for a sufficient amount of time to allow the active to act upon the surface. The method of delivery includes pre-coating the strip of material or having the wearer apply substance to the strip of material and then applying the delivery system to the teeth surfaces.

22 Claims, 3 Drawing Sheets

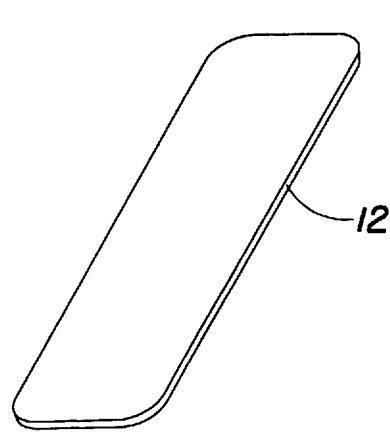
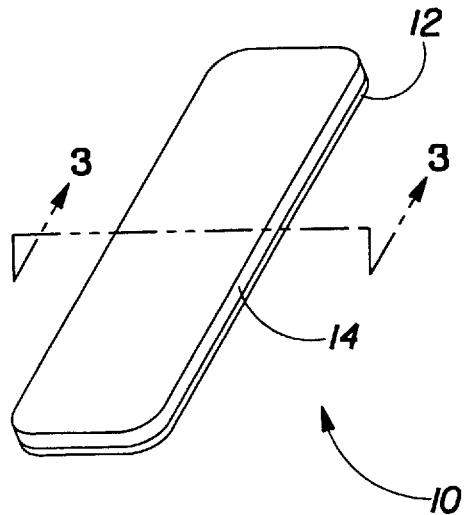
Fig. 1
Fig. 2
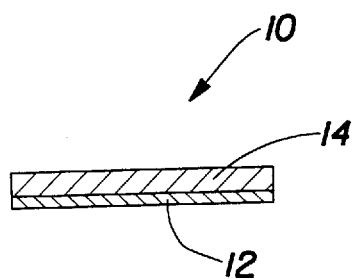
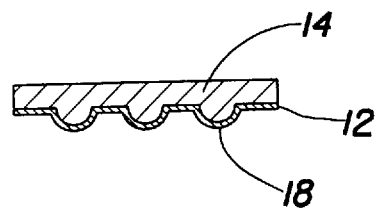
Fig. 3
Fig. 4

DELIVERY SYSTEM FOR A TOOTH WHITENER USING A STRIP OF MATERIAL HAVING LOW FLEXURAL STIFFNESS

CROSS-REFERENCE TO RELATED APPLICATIONS

This is a continuation-in-part of application Ser. No. 08/870,330, filed on Jun. 6, 1997.

FIELD OF THE INVENTION

The present invention relates to a system for the delivery of a tooth whitening substance to a plurality of adjacent teeth and more particularly to such delivery system wherein the substance is protected from erosion and interaction with saliva within the mouth for a time sufficient to enable an active provided by the substance to cause tooth whitening. The delivery system comprises a strip of material and tooth whitening substance. Even more particularly, the present invention relates to disposable delivery systems that are inexpensive and unobtrusive. The present invention also relates to a method of delivering a tooth whitening substance to a plurality of adjacent teeth.

BACKGROUND OF THE INVENTION

The most common implement for dental hygiene is the toothbrush. The mechanical action of the toothbrush bristles aids in the removal of food particles, plaque, and the like. The toothbrush is normally used with a toothpaste. Prior to about 1955, a typical toothpaste consisted of a surfactant and an abrasive material. These products were simply intended to augment the mechanical action of the brushing.

In 1955, CREST® toothpaste with fluoride, a Trademark of The Procter & Gamble Company of Cincinnati, Ohio, was introduced and the toothbrush and fluoride toothpaste combination proved to be a suitable means to deliver a fluoride treatment to the teeth surfaces. Subsequently, other active ingredients, such as tartar control agents, have been added to toothpaste to provide further dental hygiene benefits. Consumers have also turned their attention to the cosmetic aspects of dental care, such as teeth straightening and whitening.

Given the success of delivering chemicals which provide therapeutic benefits for oral care, it is reasonable to expect similar success in accomplishing the cosmetic benefit via routine brushing. However, people who are serious about whitening their teeth and who have been disappointed by the results of whitening dentifrices, often resort to professional help for whitening their teeth.

Professional teeth whitening programs provided by dentists generally fall into two categories: an in-office bleaching procedure and an outside-the-office bleaching procedure. The in-office procedure involves several visits, each of which begins with the fabrication of a specially fitted rubber dam within the mouth to prevent the bleaching chemicals, typically hydrogen peroxide, from contacting the soft oral tissue. The strength of the peroxide bleach mandates the use of the dam.

The outside-the-office bleaching program differs in that the patient applies the bleaching agent to his or her own teeth using a lower strength chemical over an extended period of time, typically several hours a day for several weeks. The outside-the-office program typically requires an initial fitting in the dentist's office for an appliance which is specific to the particular patient. The appliance is a device that is fabricated to fit precisely onto the patient's teeth and is used to deliver to the patient's teeth a bleaching gel. The patient is responsible for measuring and applying the bleaching agent to the surfaces of the teeth using the appliance as the means for delivery and containment.

Because the appliance is reused, it must be sufficiently robust to endure repeat handling, cleaning, filling, installation, and wearing. Such appliances are relatively rigid in order to maintain fit during repeat use. Typically, a patient uses the device in time periods when social contact can be avoided.

There are now non-professional programs available to persons interested in whitening their teeth using commercial products available at drug stores. The commercial products provide a kit which includes a generic appliance and a container of bleaching gel. The obvious appeal is the lower cost of the program. A major disadvantage of this "one size fits all" appliance is the greater void between the interior walls of the appliance and the teeth versus the professionally fitted appliance. Hence, in order to insure intimate contact of the bleaching gel and the teeth surfaces, more bleaching gel is required. Furthermore, the poorer fit means a greater loss of bleaching gel onto the gums, into the oral cavity, and eventual ingestion. The commercial kits, like the outside-the-office professionally administered program, require the user to clean and to reuse the appliance. Since generic appliances are not fitted to the individual user, they are even more bulky in the mouth than the fitted appliances and thus they restrict social discourse to a greater degree.

One attempt to remedy some of the problems of the commercial kits is disclosed in U.S. Pat. No. 5,575,654, issued to Fontenot on Nov. 19, 1996. Fontenot discloses a prepackaged moldable dental appliance, adapted to fit a wide range of variously sized dental arches, which contains a premeasured amount of medicinal or bleaching agent. In use, the dental appliance is removed from the packaging, aligned in a parallel fashion to the edges of the teeth and pushed over the teeth in the direction of the periodontal tissue until it covers the teeth surfaces.

Another solution is disclosed in U.S. Pat. No. 5,310,563, issued to Curtis et al. on May 10, 1994. Curtis et al. disclose a putty-like material which is formed by pressing against the teeth. It is held in place by mechanical engagement with undercut surfaces and by friction. The composition encapsulates the active.

Other methods are disclosed in U.S. Pat. No. 5,425,953, issued to Sintov et al. on Jun. 20, 1995. Sintov et al. discloses a liquid polymer composition for bleaching of the teeth. The liquid polymer composition forms a film after applied to the teeth. Other references which disclose using a film in the oral cavity include U.S. Pat. No. 4,713,243 issued to Schiraldi et al. on Dec. 15, 1987, and U.S. Pat. No. 2,835,628, issued to Saffir on May 20, 1958.

What is needed is a low cost commercial delivery system, which has a customized fit for a minimal volume of a tooth whitening substance, and which is in conformable contact with the appropriate tooth surfaces and interstitial tooth spaces for rapid delivery of an active in such substance. In addition a delivery system is needed which does not require extensive user placement manipulation to be certain of good contact. Furthermore, what is needed is a non-bulky active containment means that will permit the wearer to use the system during social discourse without interfering with the wearer's speech or appearance. Also needed is a containment means that will protect the tooth whitening substance from erosion from contact with inner mouth surfaces and saliva.

SUMMARY OF THE INVENTION

In practicing the present invention, a strip of material is applied by the wearer to a plurality of adjacent teeth. The side of the strip of material facing the tooth is coated with a tooth whitening substance. The substance is preferably in a viscous state, such as a gel, so that it provides not only the active but also tackiness between the teeth surfaces and the strip of material to hold the strip of material in place. The conformable strip of material is preferably of a size that individually fits the front 6–8 teeth of the upper or lower rows of teeth when positioned against the teeth. As a soft, conformable material, the strip may come into contact with the wearer's gums without causing physical irritation. The strip of material readily conforms to the teeth by lightly pressing it thereagainst and/or by the wearer gently sucking through the gaps between teeth. The strip of material is readily conformable without permanent deformation to the shape of the teeth when the delivery system is placed thereagainst. The strip of material is easily removed by the wearer after use by peeling it off. Preferably, each successive treatment uses a fresh strip of material.

By being a relatively thin coating, the tooth whitening substance is low in volume compared to the substance contained by rigid trays fitted or unfitted. Therefore, substance is not wasted, and little of it is accidentally ingested or otherwise available for irritation of oral cavity surfaces for which it is not intended. Preferably, the strip of material and substance are substantially transparent so as to be almost unnoticeable when worn.

The delivery system also includes the tooth whitening substance applied to the strip of material. When the delivery system is placed on the surface of the teeth, the substance contacts the surface providing an active onto the surface. The substance also provides adhesive attachment between the strip of material and the surface to hold the delivery system in place for a sufficient time to allow the active to act upon the surface. Preferably, the substance is in the form of a gel, which is a substantially uniform continuous coating on the strip of material.

In another aspect of the present invention, a method of delivering a tooth whitening substance to the surface of the teeth includes the step of applying the substance onto a conformable strip of material. This is followed by applying the conformable strip of material to the surface of the teeth without permanent deformation of the strip of material. The substance provides an active onto the surfaces and also provides adhesive attachment between the strip of material and the surface to hold the delivery system in place for a sufficient time to allow the active to act upon the surface.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 1 is a perspective view of a substantially flat strip of material having rounded corners;

FIG. 2 is a perspective view of an embodiment of the present invention, disclosing the flat strip of FIG. 1 coated with a tooth whitening substance;

FIG. 3 is a cross-sectional view thereof, taken along section line 3—3 of FIG. 2, disclosing an example of the flat strip having a thickness less than that of the substance coated thereon;

FIG. 4 is a cross-sectional view showing an alternative embodiment of the present invention, showing shallow pockets in the strip of material, which act as reservoirs for additional substance coated on the strip;

DETAILED DESCRIPTION OF THE INVENTION

Figure 5:
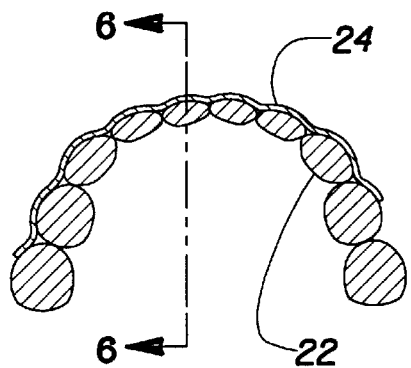
FIG. 5 is a cross-sectional view showing adjacent teeth having the strip of material of the present invention conforming thereto and adhesively attached to the teeth by means of a substance located between the teeth and the strip of material.

The abbreviation "cm", as used herein, means centimeter. The abbreviation "mm", as used herein, means millimeter.

Referring now to the drawings, and more particularly to FIGS. 1 and 2, there is shown a first preferred embodiment of the present invention, which is generally indicated as 10. Embodiment 10 represents a delivery system for a tooth whitening substance. Delivery system 10 has a strip of material 12, which is initially substantially flat, preferably with rounded corners.

Applied or coated onto strip of material 12 is a tooth whitening substance 14. Preferably, substance 14 is homogeneous, uniformly and continuously coated onto strip of material 12, as shown in FIG. 3. However, substance 14 may alternatively be a laminate or separated layers of components, an amorphous mixture of components, separate stripes or spots or other patterns of different components, or a combination of these structures including a continuous coating of oral care substance 14 along a longitudinal axis of a portion of strip of material 12.

As shown in FIG. 4, an alternative embodiment, a strip of material 12 may have shallow pockets 18 formed therein. When substance 14 is coated on a substance-coated side of strip of material 12, additional substance 14 fills shallow pockets 18 to provide reservoirs of additional substance 14.

Figure 6:
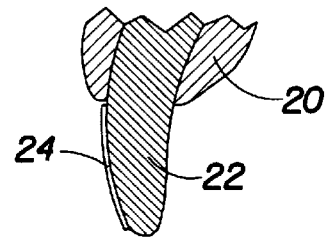
FIG. 6 is a cross-sectional elevation view of a tooth and adjoining soft tissue, taken along section line 6—6 of FIG. 5, disclosing the strip of the present invention conforming to and adhesively attached to the tooth by means of the substance located between the tooth and the strip of material.

FIGS. 5 and 6 show a delivery system 24 of the present invention applied to a plurality of adjacent teeth and the surface of a tooth. Embedded in adjacent soft tissue 20 is a plurality of adjacent teeth 22. Adjacent soft tissue is herein defined as soft tissue surfaces surrounding the tooth structure including: papilla, marginal gingiva, gingival sulculus, inter dental gingiva, gingival gum structure on lingual and buccal surfaces up to and including muco-ginival junction and the pallet.

In both FIGS. 5 and 6, delivery system 24 represents strip of material 12 and substance 14, with substance 14 on the side of strip of material 12 facing adjacent teeth 22. Substance 14 may be pre-applied to strip of material 12 or applied to strip of material 12 by the delivery system user. In either case, strip of material 12 has a thickness and flexural stiffness which enable it to conform to the contoured surfaces of adjacent teeth 22 and to adjacent soft tissue 20. The strip of flexible material has sufficient flexibility to form a curved shape around a plurality of adjacent teeth. The strip of material is also readily conformable to tooth surfaces and to the interstitial tooth spaces without permanent deformation when the delivery system is applied. The delivery system is applied without significant pressure.

Figure 7:
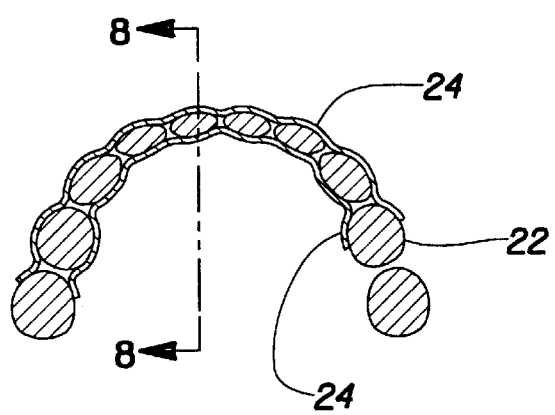
FIG. 7 is a cross-sectional view, similar to FIG. 5, showing a strip of material of the present invention conforming to the teeth and the adjoining soft tissue and adhesively attached to both sides of the teeth by means of the substance located between the teeth and the strip of material.
Figure 8:
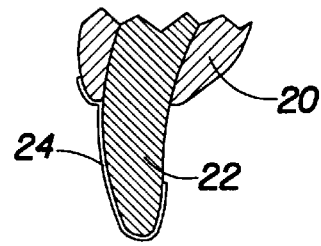
FIG. 8 is a cross-sectional elevation view, taken along section line 8—8 of FIG. 7, showing the strip of material of the present invention conforming to both the tooth and the adjoining soft tissue and adhesively attached to both sides of the tooth by means of the substance located between the tooth and the strip of material.

FIGS. 7 and 8 show delivery system 24 of the present invention applied to both front and rear surfaces of a plurality of adjacent teeth 22 as well as to adjacent soft tissue 20 located by the front surfaces of the teeth. Delivery system 24 represents strip of material 12 and substance 14, with substance 14 on the side of strip of material 12 facing adjacent teeth 22.

Figures 9, 10:
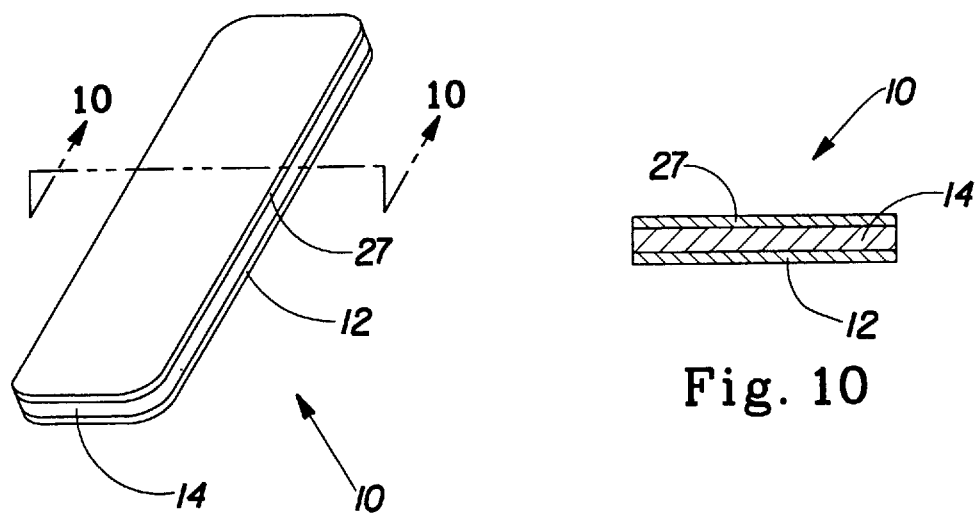
FIG. 9 is a perspective view of an alternative embodiment of the present invention, disclosing the flat strip coated with a tooth whitening substance of FIG. 2 with a release liner.
FIG. 10 is a cross-section view of an alternative embodiment of the present invention, taken along section line 10—10 of FIG. 9, showing a release liner attached to the strip of material by the substance on the strip of material.

FIGS. 9 and 10 shows a optional release liner 27. Release liner 27 is attached to strip of material 12 by substance 14. Substance 14 is on the side of strip of material 12 facing release liner 27. This side is applied to the tooth surface once release liner 27 is removed.

Strip of Material

The strip of material serves as a protective barrier to substantially prevent saliva contacting the tooth whitening substance and leaching and/or erosion of the tooth whitening substance from the surface of the teeth by the wearer's lips, tongue, and other soft tissue. In order for an active in tooth whitening substance to act upon the surface of tooth over an extended period of time, from several minutes to several hours, it is important to minimize such leaching and/or erosion. The term "act upon" is herein defined as bringing about a desired change. For example, if the substance is a tooth whitener, it bleaches color bodies to bring about whitening.

The strip of material may comprise materials such as polymers, natural and synthetic wovens, non-wovens, foil, paper, rubber, and combinations thereof. The strip of material may be a single layer of material or a laminate of more than one layer. Generally, the strip of material is substantially water impermeable. The material may be any type of polymer that meets the required flexural rigidity and is compatible with tooth whitening actives, such as peroxide. The material may comprise a single polymer or a mixtures of polymers. Suitable polymers include, but are not limited to, polyethylene, ethylvinylacetate, ethylvinyl alcohol, polyesters such as Mylar® manufactured by DuPont, fluoroplastics such as Teflon® manufactured by DuPont, and combinations thereof Preferably, the material is polyethylene. The strip of material is generally less than about 1 mm thick, preferably less than about 0.05 mm thick, and more preferably from about 0.001 to about 0.03 mm thick. A polyethylene strip of material is preferably less than about 0.1 mm thick and more preferably from about 0.005 to about 0.02 mm thick.

Preferably, the shape of the strip of material is any shape that has rounded corners. "Rounded corners" is defined as not having any sharp angles or points. The conformable strip of material is preferably of a size that individually fits the row of teeth desired to be bleached. Generally, this is the front 6–8 teeth of the upper or lower rows of teeth that are visible when the wearer is smiling. Optionally, the strip of material may fit the entire upper or lower rows of teeth when positioned against the teeth. The size of the strip of material depends upon many factors, including the number of teeth to be bleached, the size of the teeth, and personal preference of the wearer. In general, the length of the strip of material is from about 2 cm to about 12 cm and preferably from about 4 cm to about 9 cm. The width of the strip of material will also depend upon many factors, including whether or not the strip of material wraps around the teeth and covers both surfaces of the tooth. In a general application, the width of the strip of material is from about 0.5 cm to about 4 cm and preferably from about 1 to about 2 cm.

The strip of material may contain shallow pockets. When the substance is coated on a substance-coated side of strip of material, additional substance fills shallow pockets to provide reservoirs of additional substance. Additionally, the shallow pockets help to provide a texture to the delivery system. The film will preferably have an array of shallow pockets. Generally, the shallow pockets are approximately 0.4 mm across and 0.1 mm deep. When shallow pockets are included in the strip of material and substances are applied to it in various thicknesses, the overall thickness of the delivery system is generally less than about 1 mm.

Preferably, the overall thickness is less than about 0.5 mm.

Flexural stiffness is a material property that is a function of a combination of strip thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In the present invention, the strip of material has a flexural stiffness of less than about 5 grams/cm as measured on a Handle-O-Meter, model #211-300, available from Thwing-Albert Instrument Co. of Philadelphia, Pa., as per test method ASTM D2923-95. Preferably, the strip of material has a flexural stiffness less than about 4 grams/cm, more preferably less than about 3 grams/cm, and most preferably from about 0.1 grams/cm to about 1 grams/cm. Preferably, the flexural stiffness of the strip of material is substantially constant and does not significantly change during normal use. For example, the strip of material does not need to be hydrated for the strip to achieve the low flexural stiffness in the above-specified ranges.

This relatively low stiffness enables the strip of material to drape over the contoured surfaces of teeth with very little force being exerted; that is, conformity to the curvature of the wearer's mouth and gaps between adjacent teeth is maintained because there is little residual force within strip of material to cause it to return to its substantially flat shape. The flexibility of the strip enables the strip of material to contact adjoining soft tissue over an extended period of time without physical irritation. The strip of material does not require pressure forming it against the teeth.

The strip of material is held in place on a plurality of adjacent teeth by adhesive attachment provided by the substance. The viscosity and general tackiness of the substance cause the strip of material to be adhesively attached to a plurality of adjacent teeth without substantial slippage under the potential friction from the lips, tongue, and other soft tissue rubbing against the strip of material during mouth movements associated with talking, drinking, etc. However, this adhesion to the teeth is low enough to allow the delivery system to be easily removed by the wearer by peeling off the strip of material using one's finger or fingernail. The delivery system is easily removable from the surfaces of the teeth without the use of an instrument, a chemical solvent, or undue friction. Chemical solvents include any organic solvents commonly used in oral care products such as alcohol and other safe solvents such as water, which could be used to dilute the gelling agent. Undue friction is described as any type of rubbing with one's finger or a soft implement, such as cotton balls, swabs, or gauze pads.

A peel force of from about 1 gram to about 50 grams for a 1.5 cm strip width (approximately 17 grams/cm) is all that is required. Preferably, the peel force is from about 5 grams to about 40 grams and more preferably from about 10 grams to about 30 grams. The low peel force is desired for consumer handling purposes. The low peel force is possible because of the non-aggressive nature of a gel substance. Only when the flexural stiffness of the strip is low can the adhesion of the substance also be low. The adhesion of a stiffer strip would have to be greater in proportion to the strip stiffness in order to prevent the strip from returning to its flat condition and pulling away from the contoured surface of a plurality of teeth.

The strip of material may be formed by several of the film making processes known in the art. Preferably, a strip of material made of polyethylene is made by a blown process or a cast process. Processes, such as extrusion and other processes that do not affect the flexural rigidity of the strip of material, are also feasible. Additionally, the substance may be incorporated onto the strip during the processing of the strip. The substance may be a laminate on the strip.

Tooth Whitening Substance

The tooth whitening substance is a composition, compound, or mixture capable of influencing or effecting a desired change in appearance and/or structure of the surface it contacts. Examples of appearance and structural changes include, but are not necessarily limited to, whitening, stain bleaching, stain removal, plaque removal, and tartar removal. Preferably, the active is for the whitening of the tooth surfaces.

The amount of substance applied to the strip of material or teeth will depend upon the size and capacity of the piece of material, concentration of the active, and the desired benefit. Generally, less than about 1 gram of substance is required. Preferably, from about 0.05 grams to about 0.5 grams and more preferably from about 0.1 gram to about 0.4 grams of the substance is used. The amount of substance per square cm of material is less than about 0.2 grams/cm$^2$, preferably from about 0.005 to about 0.1 grams/cm$^2$, and more preferably from about 0.01 grams/cm$^2$ to about 0.04 grams/cm$^2$.

The substance of the present invention can be in the form of a viscous liquid, paste, gel, solution, or other suitable form that can provide sufficient adhesion. Preferably, the substance is in the form of a gel. The substance will have a viscosity of from about 200 to about 1,000,000 at low shear rates (less than one 1/seconds). Preferably, the viscosity is from about 100,000 to about 800,000 cps and more preferably from about 400,000 to about 600,000 cps.

Actives suitable for whitening include any material safe for use in the oral cavity which provides bleaching or stain removal. The actives suitable for whitening are selected from the group consisting of the peroxides, metal chlorites, perborates, percarbonates, peroxyacids, and combinations thereof. Suitable peroxide compounds include hydrogen peroxide, calcium peroxide, carbamide peroxide, and mixtures thereof. Most preferred is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. The preferred chlorite is sodium chlorite.

The tooth whitening active is present in an amount of from about 0.01% to about 40%, by weight of the substance. If a peroxide compound is chosen as the active, the peroxide compound should provide an amount of hydrogen peroxide equivalent of from about 0.1% to about 20%, preferably from about 0.5% to about 10%, and most preferably from about 1% to about 7%, by weight of the substance. To deliver this amount of hydrogen peroxide equivalent, the peroxide compound, such as carbamide peroxide, is generally present in an amount of from about 0.1% to about 30% and preferably from about 3% to about 20%, by weight of the substance.

The actives are generally contained in an aqueous gel. The gel is a high viscosity matrix formed from gelling agents known in the art. These gelling agents are safe for oral use, do not readily dissolve in saliva, and do not react with or inactivate the oral care compounds incorporated into them. Generally, the gelling agent is a swellable polymer. Furthermore, the gel formed with these agents provides sufficient adhesive attachment of the film material to the targeted area of the mouth. The level of gelling agent to form the gel composition is from about 0.1% to about 15%, preferably from about 1% to about 10%, more preferably from about 2% to about 8%, and most preferably from about 4% to about 7%, by weight of the substance.

Suitable gelling agents useful in the present invention include carboxypolymethylene, carboxymethyl cellulose, carboxypropyl cellulose, poloxamer, carrageenan, Veegum, carboxyvinyl polymers, and natural gums such as gum karaya, xanthan gum, Guar gum, gum arabic, gum tragacanth, and mixtures thereof. The preferable gelling agent for use in the present invention is carboxypolymethylene, obtained from B. F. Goodrich Company under the tradename "Carbopol". Particularly preferable Carbopols include Carbopol 934, 940, 941, 956 and mixtures thereof. Particularly preferred is Carbopol 956. Carboxypolymethylene is a slightly acidic vinyl polymer with active carboxyl groups. The normal concentration of various carboxypolymethylene resins in water, according to the manufacturer, is below about 2%. However, it has been found that by preparing supersaturated carboxypolymethylene compositions having an absolute concentration in the ranges specified above, suitable high viscosity oral gel compositions may be prepared.

The concentrated carboxypolymethylene gels have a number of important characteristics in addition to high viscosity. Enough carboxypolymethylene is added to the oral gel compositions beyond that required to provide high viscosity such that a significant quantity of saliva or water is required to lower the viscosity to the point that the composition may be diluted and washed out by saliva. The concentrated carboxypolymethylene composition also has a unique tackiness or stickiness which retains and seals the strip material against the targeted oral cavity surface it is affixed to, particularly teeth. However, care should be taken to avoid too much carboxypolymethylene thereby making insertion or withdrawal of the strip material difficult.

Water is also present in the gel compositions disclosed herein. The water, employed in the present invention should, preferably, be deionized and free of organic impurities. Water comprises from about 0.1% to 95%, preferably from about 5% to about 90%, and most preferably from about 10% to about 80%, by weight of the substance. This amount of water includes the free water that is added plus that amount that is introduced with other materials.

A pH adjusting agent may also be added to optimize the storage stability of the gel and to make the substance safe for oral tissues. These pH adjusting agents, or buffers, can be any material which is suitable to adjust the pH of the substance. Suitable materials include sodium bicarbonate, sodium phosphate, sodium hydroxide, ammonium hydroxide, sodium stannate, triethanolamine, citric acid, hydrochloric acid, sodium citrate, and combinations thereof. The pH adjusting agents are added in sufficient amounts so as to adjust the pH of the gel composition to about 4.5 to about 11, preferably from about 5 to about 8.5, and more preferably from about 5.5 to about 7. pH adjusting agents are generally present in an amount of from about 0.01% to about 15% and preferably from about 0.05% to about 5%, by weight of the substance.

While the gel described above provides sufficient adhesiveness, additional gelling agents may also be included in the formula to help the active ingredients adhere to the tissues of the oral cavity. Suitable agents include both polymers with limited water solubility as well as polymers lacking water solubility. These polymers deposit a thin film on both the oral cavity's soft and hard tissues when saliva combines with the instant composition. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

An additional carrier material may also be added to the substance. Carrier materials can be humectants. Suitable humectants include glycerin, sorbitol, polyethylene glycol, propylene glycol, and other edible polyhydric alcohols. Humectants are generally present in an amount of from about 10% to about 95%, preferably from about 20% to about 80%, and more preferably from about 50% to about 70%, by weight of the substance. In addition to the above materials of the gel of the present invention, a number of other components can also be added to the substance. Additional components include, but are not limited to, flavoring agents, sweetening agents, xylitol, opacifiers, coloring agents, and chelants such as ethylenediaminetetraacetic acid. These additional ingredients can also be used in place of the compounds disclosed above.

Release Liner

The release liner may be formed from any material which exhibits less affinity for substance than substance exhibits for itself and for the strip of material. The release liner preferably comprises a rigid sheet of material such as polyethylene, paper, polyester, or other material which is then coated with a non-stick type material. The release liner material may be coated with wax, silicone, polyester such as Teflon®, fluoropolymers, or other non-stick type materials. A preferred release liner is Scotchpak®, produced by 3M. The release liner may be cut to substantially the same size and shape as the strip of material or the release liner may be cut larger than the strip of material to provide a readily accessible means for separating the material from the strip. The release liner may be formed from a brittle material which cracks when the strip is flexed or from multiple pieces of material or a scored piece of material. Alternatively, the release liner may be in two overlapping pieces such as a typical adhesive strip bandage type design. A further description of materials suitable as release agents is found in Kirk-Othmer Encyclopedia of Chemical Technology, Fourth Edition, Volume 21, pp. 207–218, incorporated herein by reference.

EXAMPLES

The strip of material is preferably a 0.013 mm thick piece of polyethylene film. The film preferably has an array of shallow pockets, typically 0.4 mm across and 0.1 mm deep. The strip of material has a flexural stiffness of about 0.6 grams/cm as measured on a Handle-O-Meter, model #211–300, available from Thwing-Albert Instrument Co. of Philadelphia, Pa., as per test method ASTM D2923-95.

An example of a tooth whitener is a gel described as follows: Combine 70% glycerin, 5% carboxypolymethylene, 10% carbamide peroxide, and 15% water adjusted to pH 6.5 with sodium hydroxide. Mix until homogeneous.

Additional examples of alternative tooth whitening gel are described as follows: Combine 8% carboxypolymethylene in approximately 84% water, add 4% sodium hydroxide and enough sodium bicarbonate to bring the pH to about 10. Dissolve in 3.75% sodium chlorite and mix until homogeneous.

Combine 56% glycerin, 6% carboxypolymethylene, 10% carbamide peroxide, and 24% water. Add 4% sodium hydroxide (50% solution) to adjust the pH. Mix until homogeneous.

Combine 68% glycerin, 6% carboxypolymethylene, 22% carbamide peroxide, and 4% sodium hydroxide (50% solution). Mix until homogeneous.

Combine 25% glycerin, 69.7% water, 2% xanthan gum, 3% carboxymethylcellulose, and 0.3% carbamide peroxide. Mix until homogeneous.

Combine 24% poloxamer, 20% glycerin, 46% polyethylene glycol, and 10% carbamide peroxide. Mix until homogeneous.

Commercial tooth whiteners, such as Opalescence and Nu-Pro Gold, are also operable with the delivery system of the present invention.

Method of Use

In practicing the present invention, a strip of material is applied by the wearer to a plurality of adjacent teeth. The side of the material facing the teeth is coated with a tooth whitening substance which is preferably in a viscous state to provide not only the active but also tackiness between the tooth surfaces and the strip of material to hold the strip in place for an extended period of time. The strip of material readily conforms to the teeth by lightly pressing it against the teeth and/or by the wearer gently sucking through the gaps between the teeth. The strip of material is easily removed by the wearer by peeling it off. Preferably, each successive treatment will use a fresh strip of material.

The tooth surface is not required to be prepared before the delivery system is applied. For example, the wearer may or may not choose to brush his teeth or rinse his mouth before applying the delivery system. The surfaces of the teeth are not required to be dried or to be excessively wet with saliva or water before the strip of material is applied.

Preferably, the strip of material and substances are substantially transparent so as to be almost unnoticeable when worn. Thinness of the delivery system enables the higher temperature inside of the wearer's mouth to conduct heat through the strip of material to the normally cooler teeth in order to accelerate the rate of diffusion of the active material into the surfaces of the teeth.

Preferably, the wearer applies the delivery system of the present to the teeth continuously for about 5 minutes to about 120 minutes a day, preferably from about 30 minutes to about 60 minutes. Generally, this is done once a day for about 7 to 28 days. The amount of time and the number of days are dependent upon several factors, including the amount of bleaching desired, the wearer's teeth, and if initial or maintenance bleaching is desired. The bleaching is done to achieve a whitening benefit of 1–4 shade guide improvement as measured by VITA LUMIN® Vacuum Farbskala Shade Guides, a product of VITA Zahnfabrik, of BadSackingen, Germany.

When the wearer removes the strip of material from the tooth, there may be a residue of substance remaining on the surface. This residual will not be great, as the tooth whitening substance has affinity for both the film and for itself. If residual substance remains, it may be easily removed by brushing or rinsing.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A delivery system for delivering a tooth whitening substance to front side of a plurality of adjacent teeth wherein the delivery system is substantially transparent and is almost unnoticeable when worn, said delivery system comprising:
   a. a strip of flexible material having a sufficient flexibility to form a curved shape on a plurality of teeth, said strip of material being readily conformable to tooth surfaces and to interstitial tooth spaces without permanent deformation when said delivery system is placed thereagainst; and
   b. a tooth whitening substance applied to said strip of material such that when said delivery system is placed on a surface of said teeth, said substance contacts said surface providing an active onto said surface, said substance also providing adhesive attachment between said strip of material and said surface to hold said delivery system in place for a sufficient time to allow said active to act upon said surface.

2. The delivery system of claim 1 wherein said strip has a substantially constant flexural stiffness of less than about 5 grams/centimeter as measured on a Handle-O-Meter per ASTM test method D2923-95.

3. The delivery system of claim 2 wherein said strip of material is comprised of materials which are compatible with one or more tooth whitening actives.

4. The delivery system of claim 3 wherein said strip of material is capable of recovery from said deformed state in the absence of adhesive forces due to said tooth whitening substance.

5. The delivery system of claim 4 wherein said strip of material is substantially water impermeable.

6. The delivery system of claim 3 wherein said substance is a gel.

7. The delivery system of claim 6 wherein said substance is a substantially uniform continuous coating on said strip of material.

8. The delivery system of claim 6 where said tooth whitening active in said substance is selected from the group consisting of peroxides, metal chlorites, perborates, percarbonates, peroxyacids, and combination thereof.

9. The delivery system of claim 8 wherein said strip of material and said substance applied thereon have an overall thickness less than about 1 mm.

10. The delivery system of claim 9 wherein said strip of material with said substance has a peel force of less than 50 grams.

11. The delivery system of claim 9 wherein said strip of material with said substance is removable from said tooth surface without the use of an instrument, a chemical solvent, or undue friction.

12. The delivery system of claim 3 wherein the delivery system is applied to adjoining soft tissue of said plurality of teeth in addition to said tooth surfaces.

13. The delivery system of claim 13 wherein the said tooth surface are not required to be prepared before application of said delivery system.

14. The delivery system of claim 3 wherein said strip of material has shallow pockets on a substance-coated side of said strip of material, said shallow pockets having a substance located therein.

15. The delivery system of claim 6 where said substance comprises an amount of carboxypolymethylene from about 0.5% to about 12%, by weight of the substance.

16. The delivery system of claim 15 wherein said substance comprises an amount of water from about 0.1% to about 95%, by weight of the substance.

17. The delivery system of claim 16 wherein said strip of material is a polyethylene film having a nominal film thickness of less than about 0.1 mm.

18. The delivery system of claim 3 further comprising a release liner.

19. A method of delivering a tooth whitening substance to front side of a plurality of adjacent teeth, said method comprising the steps of:
   a. applying said substance onto a comfortable strip of material having a sufficient flexibility to form a curved shape around a plurality of adjacent teeth and said strip of material being readily conformable to tooth surfaces and to interstitial tooth spaces without permanent deformation; and
   b. applying said conformable strip of material with said substance thereon to said plurality of adjacent teeth without permanent deformation of said strip of material such that said substance contacts said surface, said substance providing an active onto said plurality of adjacent teeth, said substance also providing adhesive attachment between said strip of material and said plurality of adjacent teeth to hold said delivery system in place for a sufficient time to allow said active to act upon said surface.

20. A delivery system for delivering a tooth whitening substance to a plurality of adjacent teeth, said delivery system comprising:
   a. a strip of flexible material having a sufficient flexibility to form a curved shape on a plurality of adjacent teeth, said strip of material being readily conformable to tooth surfaces and to interstitial tooth spaces without permanent deformation when said delivery system is placed thereagainst and said strip of material containing an array of shallow pockets; and b. a tooth whitening substance applied to said strip of material such that when said delivery system is placed on a surface of said teeth, said substance contacts said surface providing an active onto said surface, said substance also providing adhesive attachment between said strip of material and said surface to hold said delivery system in place for a sufficient time to allow said active to act upon said surface.

21. A delivery system for delivering a tooth whitening substance to a plurality of adjacent teeth, said delivery system comprising:

a. a strip of flexible material having a sufficient flexibility to form a curved shape on a plurality of adjacent teeth, said strip of material being readily conformable to tooth surfaces and to interstitial tooth spaces without permanent deformation when said delivery system is placed thereagainst;

b. a tooth whitening substance applied to said strip of material such that when said delivery system is placed on a surface of said teeth, said substance contacts said surface providing an active onto said surface, said substance also providing adhesive attachment between said strip of material and said surface to hold said delivery system in place for a sufficient time to allow said active to act upon said surface; and c. a release liner.

22. A delivery system for delivering a tooth whitening substance to a plurality of adjacent teeth, said delivery system comprising:

a. a strip of flexible material made of polyethylene; and b. a tooth whitening substance applied to said strip of material such that when said delivery system is placed on a surface of said teeth, said substance contacts said surface providing an active onto said surface, said substance also providing adhesive attachment between said strip of material and said surface to hold said delivery system in place for a sufficient time to allow said active to act upon said surface.

* * * * *